United States Patent [19]

Roberts

[11] Patent Number: 4,868,161

[45] Date of Patent: Sep. 19, 1989

[54] METHOD FOR PROMOTING NERVE REGENERATION

[75] Inventor: Eugene Roberts, Monrovia, Calif.

[73] Assignee: City of Hope, Duarte, Calif.

[21] Appl. No.: 97,302

[22] Filed: Sep. 14, 1987

Related U.S. Application Data

[63] Continuation of Ser. No. 626,523, Jun. 29, 1984, abandoned.

[51] Int. Cl.$^4$ .................. A61K 31/70; A61K 31/505; A61K 31/17; A61K 33/40
[52] U.S. Cl. ........................................ 514/49; 514/50; 514/260; 514/588; 424/616
[58] Field of Search .................. 514/49, 50, 260, 588; 424/130

[56] References Cited

U.S. PATENT DOCUMENTS

| | | |
|---|---|---|
| 3,984,414 | 10/1976 | Esanu . |
| 4,073,895 | 2/1978 | Esanu . |
| 4,094,973 | 6/1978 | Robertson ........................... 424/177 |
| 4,141,973 | 2/1979 | Balazs ................................. 424/180 |
| 4,267,181 | 5/1981 | Esanu .............................. 544/330 X |
| 4,376,071 | 3/1983 | Jennings et al. ................. 260/112 R |
| 4,476,119 | 10/1984 | Roberts ............................... 424/180 |
| 4,652,554 | 3/1987 | Chwang ............................... 514/49 |

OTHER PUBLICATIONS

Chen et al., The Chemical Abstracts, 77: 13927x, (1972).
Billingsley et al., The Chemical Abstracts, 106:12875j, (1987).
Aguayo et al., The Chemical Abstracts, 84:54774h, (1976).
Carlson et al., The Chemical Abstracts, 91:117964n, (1979).
Billingsley et al., The Chemical Abstracts, 97:174642d, (1982).
Gullberg et al., Eur. J. Immunol., 13, 719–725, (1983).
Alberts et al., Molecular Biology of the Cell, pp. 570, 897 and 1016–1017, (1983).
Kuras et al., Influence of 1-$\beta$-D-arabinofuranosylcytosine on Mitotic Activity of Apical Meristem of Onion (Allium cepa L.), Roots, Chem. Abstracts 90:116324w, (1978).
Herskowitz, Principles of Genetics, p. 578, (2nd Ed., 1977).
Thomas, The Role of Bicarbonate, Chloride, and Sodium Ions in the Regulation of Intracellular pH in Snail Neurons, Chem. Abstracts, 88:19320t, (1978).
Taber's Cyclopedic Medical Dictionary, "Nerve", p. 944, (1981).
Buechner et al., Cell Kinetic Effects of Cytosine Arabinoside . . . In Vitro and In Vivo, Chem. Abstracts, 87:62452d, (1977).
Buechner et al., Cell Kinetic Response to Cytosine Arabinoside in the L5222 Rat Leukemia, Chem. Abstracts, 89:209051z, (1978).
Guth et al., J. Neurosurg., 52; 73–86, (1980).
Llinas et al., Federation Proceedings 40; No. 8; 2240–45, (1981).
Nye, Nature, 309; 406–407, May 31, 1984.

*Primary Examiner*—John W. Rollins
*Attorney, Agent, or Firm*—Edward S. Irons

[57] ABSTRACT

A method for promoting regeneration of damaged nerve tissue, comprising administering, either alone or in combination, an effective amount of an antimitotic agent or a proton-withdrawing buffer to the damage site. Antimitotic agents reduce the rate of growth of glial cells, and buffers facilitate the growth of nerve tissue and inhibit glial cell growth. Referred antimitotic agents are cytosine arabinoside, 5-fluorouracil, and hydroxyurea. Preferred buffers are TREA and HEPES. Compositions are disclosed which include antimitotic agent, buffer, and an oxygen-supplying compound, such as hydrogen peroxide.

12 Claims, No Drawings

METHOD FOR PROMOTING NERVE REGENERATION

This application is a continuation of Ser. No. 626,523, filed June 29, 1984, now abandoned.

BACKGROUND OF THE INVENTION

This invention relates to a method and compositions for promoting nerve regeneration.

Neurons are postmitotic cells which do not ungergo cell division or mitosis and accordingly are resistant to antimitotic agents. Neurons are closely associated with and surrounded by glial cells or astrocytes which proliferate and are susceptible to antimitotic agents. One of the difficultues in achieving regeneration of nerve fibers after they have been damaged or severed is that the glial cells proliferate and form a barrier to the regenerating nerve fibers. The result is that the further movement of the fibers toward anticipated attachment sites is blocked and regeneration of structure and function ceases.

Oxygen is vital to the normal function and development of nerves. If oxygenation can be increased, this will favor new growth. As demonstrated by R. Llinas, et al., Fed. Proc. 40, #8, 2240–45 (1981), $H_2O_2$ in mammalian Ringer's solution can favor nerve survival and vitality.

SUMMARY OF THE INVENTION

In accordance with the present invention, I have discovered that antimitotic agents may be used to modulate the growth of glial cells. By administering an effective amount of antimitotic agent to the site of nerve damage or injury, the growth of glial cells can be inhibited, permitting unimpeded growth of nerve tissue.

Accordingly, one aspect of the present invention is a method for promoting regeneration of damaged nerve tissue in a mammal (such as a human), comprising administering an effective amount of antimitotic agent to the damage site. The appropriate amount of antimitotic agent is an amount sufficient to reduce the rate of growth of glial cells to the extent that glial cell growth does not prevent nerve tissue growth. The antimitotic agent is administered in a concentration of about 3 to about 20 micromolar. Preferred antimitotic agents are cytosine arabinoside, 5-fluorouracil, hydroxyurea, and methotrexate.

In areas of nerve injury where blood supply is limited and edema develops, an excess of protons and a low pH usually occurs. I have discovered that proton-withdrawing substances, herein generically referred to as "buffers", serve to inhibit growth of glial tissue when used to remove protons and increase the pH at the site of a nerve injury. In addition, such buffers unexpectedly promote membrane fluidity, metabolic transport, transport of γ-aminobutyric acid (GABA), calcium transport, and other membrane functions in neural tissue. I have also discovered that, as an apparent result of these membrane-enhancing properties, buffers facilitate and promote the growth and repair of damaged nerve tissue and promote the availability of oxygen at the damage site.

The present invention also includes a method for promoting regeneration of damaged nerve tissue in a mammal, comprising the step of increasing the pH at the damage site to between about 7 and 8, and preferably to about 7.3. The pH is increased by administering a buffer (proton-withdrawing agent) to the damage site. The buffer is preferably administered in a solution or composition having a buffer concentration of between about 0.5 and about 20 millimolar, and preferably between about 1.5 and about 8 millimolar. Preferred buffers or proton-withdrawing substances include HEPES and TREA.

In the preferred embodiment of the present invention, the method for promoting regeneration of damaged nerve tissue comprises administering both an antimitotic agent and a buffer to the damage site. It is also preferred that an oxygen-supplying substance, such as any of the pharmacologically-acceptable peroxides, and particularly hydrogen peroxide, be administered with the buffer and/or antimitotic agent to the damage site. An appropriate concentration for hydrogen peroxide is 0.002% to 0.005% by volume.

The present invention also includes pharmaceutical compositions for promoting regeneration of damaged nerve tissue, comprising a pharmacologically-acceptable carrier and an antimitotic agent in the carrier in a concentration of about 3 to about 20 micromolar. Preferred antimitotic agents are cytosine arabinoside, 5-fluorouracil, hydroxyurea, and methotrexate.

Another composition falling within the present invention is a pharmaceutical composition for promoting regeneration of damaged nerve tissue, comprising a pharmacologically-acceptable carrier and a buffer, preferably HEPES or TREA, having a concentration between about 0.5 and about 20 millimolar.

A preferred composition according to the present invention includes both an antimitotic agent and a buffer in the concentrations and of the types described above.

The composition of the present invention may also include an oxygen-supplying compound, such as hydrogen peroxide, preferably in a concentration of from about 0.002% to about 0.005%.

Through use of the methods and compositions of the present invention, the growth of neurons and glial cells can be modulated by buffers and antimitotic agents applied under suitable conditions and growth of nerve fibers can be directed in an orderly fashion to achieve nerve regeneration. In situations where there is great nerve damage or transection, whether in central or peripheral nervous systems, conditions are developed which inhibit the proliferation of glial cells sufficiently to block extensive growth yet allow adequate growth for scaffolding on which orderly development can proceed, and favor the regeneration of nerve fibers.

DETAILED DESCRIPTION OF THE INVENTION

Suitable antimitotic agents may be selected, e.g., from the various folate inhibitors, such as methotrexate; pyrimidine analogs, such as cytosine arabinoside, 5-fluorouracil, floxuridine, N-phosphonoacetyl-L-aspartate, azauridine, azaribine, and idoxuridine; purine analogs, such as mercaptopurine and thioguanine; alkylating agents, such as nitrogen mustards, dacarbazine, carmustine, lomustine, and semustine; antibiotics, such as dactinomycin, daunorubicin, doxorubicin, and bleomycins; and other antiproliferative agents, such as cisplatin, hydroxyurea, and guanazole. Particularly preferred antimitotic agents are hydroxyurea, cytosine arabinoside, methotrexate, and 5-fluorouracil.

Buffers (proton-withdrawing compounds) useful in increasing pH and thereby inhibiting or regulating the growth of glial cells include: ACES, 2[2-amino-2-oxoethyl)-amino] ethanesulfonic acid; ADA, N-2(2-acetamido)-2-iminodiacetic acid; AEPD, 2-amino-2-ethyl-1,3,-propanediol; AMP, 2-amino-2-methyl-1-propanol; AMPD, 2-amino-2-methyl-1,3-propanediol; BES, N,N-bis (2-hydroxyethyl)-2-aminoethanesulfonic acid; BICINE, N-N-bis(2-hydroxyethyl)-glycine; BIS-TRIS bis(2-hydroxyethyl)-imino-tris(hydroxymethyl) methane; BIS-TRIS PROPANE, 1,3,bis[tris(hydroxymethyl)methylamino]propane; DEA, diethanolamine; EPPS, N-(2-hydroxyethyl)-1-piperazinepropanesulfonic acid; HEPES, N-2-hydroxyethylpiperazine-N'-2ethanesulfonic acid; MEA, monoethanol-amine; MES, 2-(N-morpholino)ethanesulfonic acid; MOPS, 3-(N-morpholino) propanesulfonic acid; PIPES, piperazine-N,N'-bis(2-ethanesulfonic acid); TAPS, tris(hydroxymethyl)methylaminopropanesulfonic acid; TES, N-tris(hydroxymethyl)-methyl-2-aminoethanesulfonic acid; TREA, triethanolamine; TRICINE, N-tris(hydroxymethyl)methylglycine; and TRIS, tris(hydroxymethyl)aminomethane.

Preferred buffers are TREA, HEPES, and TRIS.

The amounts of these substances considered useful as promoters of nerve regeneration varies according to the concentration necessary to inhibit glial cell growth, but would generally be in the range of 3 to 20 micromolar for antimitotic agents, and in the range of 0.5 to 20 millimolar for buffers and other proton withdrawing substances.

The efficacy of various buffers at pH 7.3 (physiological pH) on a molar basis is directly related to the concentration of the unprotonated form. This accounts for differences between buffers with different values of pKa on a total molar basis, those with higher values being less effective because of smaller concentration of unprontonated form at any given pH. The concentrations of unprontonated form found to be effective are between $1 \times 10^{-5}$ M and $1 \times 10^{-3}$ M, preferably around $2-8 \times 10^{-4}$ M.

Pharmaceutical compositions suitable for application to humans and animals with damaged or severed nerves include sterile isomolar preparations of antimitotic agents with representative proton scavengers and buffers. The antimitotic agents would normally be available in the range of 3 to 20 micromolar and would preferably be buffered to a pH of 7-8, with a pH 7.3 considered optimal.

The pharmaceutical compositions may be in the form of solutions, gels, aqueous or oily suspensions, emulsions, creams and powders. Sterile isotonic saline solutions may advantageously be used as a vehicle for the compositions of the present invention.

It is important that these compositions be administered to the damage site. From the foregoing discussion, it is apparent that the compositions of the present invention can be administered topically, transdermally, intrathecally, by injection, and by slow perfusion through silicone tubing.

EXAMPLE 1:

The Effects Of TREA, HEPES, TRIS, and Cytosine Arabinoside on Chick Embryo Peripheral Ganglia In Vitro

Methods

The simplest model in which to test the effects of nerve-growth promoting substances are excised chick embryo ganglia maintained in tissue culture. These ganglia are known to respond to nonamolar concentrations of nerve growth factor (NGF).

Dorsal root ganglia (DRG), trigeminal, and sympathetic ganglia from 7-8 day chick embryos were dissected in Dulbecco's phosphate buffered saline (Gibco), and cultured in the presence of different concentrations of triethanolamine (TREA), HEPES and TRIS buffers. It was determined that concentrations of 2.5 and 5 mM of each buffer stimulated the maximal response of neurite extension. Thereafter, DRG were used exclusively for the rest of the experiments.

Six DRG were placed in individual 60 mm culture dishes (Falcon 3002). In the normal culture condition series, 5 ml complete medium was added to each dish. This medium contained 85% Dulbecco's Modified Eagles' Medium, 10% dialyzed fetal bovine serum (both from Gibco), 3% glucose (600 mg% final), 1% glutamine (200 mM final) and 1% penicillin-streptomycin mix (Gibco). Each set of experiments which was repeated 3-4 times consisted of 2-4 dishes per treatment. All dishes were incubated for 3 days at 39° C. For each day's experiment, a control group (untreated) and a group treated with nerve growth factor (NGF) at a final concentration of 10 nM were run in parallel with the buffer-treated groups.

Each buffer was prepared as a 10 X stock solution by dissolving the buffer in complete medium and adjusting the pH to 7.2-7.4. In every series, TREA, HEPES, and TRIS were tested at final concentrations of 2.5 mM and 5.0 mM.

A series of ganglia also was run by adding cytosine arabinoside (ara C; Cytosar, Upjohn) at a final concentration of 27 micromolar in the complete medium. The various buffers, or NGF were added, or direct current applied, to the DRG in this ara C media.

Fiber Index: Neurite Outgrowth

Neurite outgrowth was determined in cultures after 3 days in vitro after fixation in 3.5% glutaraldehyde. The scoring technique is that of Fenton, E. L., Exp. Cell Res. 59:383 (1970). The scoring system ranges from 0 to +5 and is based on the neurite outgrowth observed in standard NGF cultures. Using NGF, most observers note the maximal response after 3-6 days in vitro; the response is more variable at 9 days. However, we have used this later time point in experiments in which we determined long term effects with a Cajal silver strain to substantiate phase microscopy scoring of the neurite outgrowth.

The first experiments involved the culturing of various peripheral ganglia in the presence of concentrations of TREA from 1-10 mM. It was determined that trigeminal, dorsal root, and sympathetic ganglia all responded by elaborating neuritic processes at concentrations of 2.5 and 5 mM. In contrast to control trigeminal ganglia, trigeminal ganglia cultures in 5 mM TREA or 2.5 mM TREA and sympathetic ganglia cultured in 2.5 mM TREA all demonstruated long, filamentous neuritic processes extending from the centrally-located neuronal cell bodies out to and byond the mat of underlying nonneuronal cells. Semi-quantitative assessment of neurite outgrowth was determined in the series of experiments conducted on dorsal root ganglia in complete media. The scoring of these cultures was: control, +1 response; NGF, +5 response; 5 mM TREA, +3.5 response. The data obtained from the entire series are summarized in Table 1. In all cases, significance of effect was determined using a Dunnett's Multicomparison of Treatment Means with a control test with a p limit of 0.01. Significant increase in neurite extension was obtained with all treatments.

Constant incubation in the presence of cytosine arabinoside (ara C) significantly increased the neurite outgrowth in control cultures relative to that obtained in the absence of the drug. While the number of non-neural cells was markedly depleted in cultures containing ara C, neurite extension was enhanced both in the controls and in the ganglia maintained in 5 mM TREA.

TABLE 1

Neurite Extension in Chick Embryo Ganglia

| Test Sample | | Fiber Index (Numbers of ganglia used in each experiment are shown in parentheses.) | | p value vs. Control* |
|---|---|---|---|---|
| | | Mean | S.D. | |
| Control | | 1.53 (16) | 0.74 | — |
| NGF | $10^{-8}$ M | 4.42 (19) | 1.07 | 0.001 |
| TREA | 2.5 mM | 3.07 (28) | 1.03 | 0.001 |
| | 5.0 mM | 3.42 (32) | 1.21 | 0.001 |
| HEPES | 2.5 mM | 2.66 (18) | 1.17 | 0.001 |
| | 5.0 mM | 3.18 (29) | 0.89 | 0.001 |
| TRIS | 2.5 mM | 2.55 (17) | 0.86 | 0.001 |
| | 5.0 mM | 2.55 (17) | 0.61 | 0.001 |
| Ara C | 27 Micromoles | 3.10 (45) | 0.72 | 0.001 |

*In unsupplemented culture medium, which contained 85% Dulbecco's Modified Eagle's medium, 10% dialyzed fetal bovine serum, 3% glucose, 1% glutamine, and 1% penicillin - streptomycin mix.

EXAMPLE 2:

The Effects Of Trea and Cytosine Arabinoside On Regeneration After Spinal Cord Injury in the Rat Much current data leave little question that there is an inherent capacity of the injured mammalian central nervous system to undergo some growth and repair. However, formation of astrocytic and connective tissue scars and progressive necrosis are serious impediments to effective regeneration and reinstitution of function. All past efforts to develop treatments that will stimulate tissue repair and regeneration have been unsuccessful because of failure to correct the complex and incoordinated histopathological response of the spinal cord to injury. We now have adopted a more systematic approach in which a histologically-reproducible model of spinal cord injury is utilized and treatments are employed which bring back into balance the relationships between the nerves and their supporting cells, the glial and ependymal cells, and connective tissue elements.

Method

The dura was opened and a polyethylene tube was sutured to the vertebral spines and adjacent soft tissues so that the opening in one end lay directly over the injured part of the spinal cord. The tubing was brought through a subcutaneous tunnel so that its other end emerged at the base of the skull. A syringe adapter was attached to the external opening for injecting the drugs. In preliminary experiments it was ascertained that if the dura was opened within two days of a crash injury, edema was still present and resulted in a herniation-like protrusion of the substance of the core and damage to this fragile tissue. Accordingly, we adopted the procedure of waiting two days after crushing the cord, at which time we reoperated on the animal, opened the dura, implanted the tube, and commenced the treatment. The drugs were administered four times a day in volumes of 0.5 ml which was found sufficient to thoroughly flood the site of injury. All experiments were done on a double blind basis and three animals each were respectively treated with 10 millimolar TREA; 6 micromolar cytosine arabinoside; 10 millimolar TREA containing 6 micromolar cytosine arabinoside; and the buffered saline vehicle. Treatment of every animal was continued for 14 days, after which the animals were killed and histological sections prepared. The histological preparations were independently evaluated by three scientists experienced in this field.

Results

The results of the study were remarkably consistent. In every case the drug treated animals showed remarkably greater invasion of the lesion by nerve fibers than did the vehicle treated control animals. In fact, there was no obvious difference between the saline-treated control specimens and the untreated animals. In the drug-treated animals, the nerve fibers grew into the lesion site in such profusion that they were no longer oriented longitudinally, but grew rather haphazardly in all directions. Fibers were frequently undulating and varicose and were often arranged in small bundles containing 3-6 axons. The axons were very fine in caliber, most of them being 1-4 microns in diameter. Since they were so close to the resolution of the light microscope, we suspect that considerably greater invasion would be seen by electron microscopy. When the slides were coded and randomized, there was no difficulty in distinguishing between the specimens from the drug-treated and the vehicle-treated animals.

The most prolific nerve growth occurred in the animals treated with cytosine arabinoside and TREA. The animals treated with either TREA or cystosine arabinoside also exhibited extensive nerve growth in comparison to the control.

Examples 3-8 detail the preparation of pharmaceutical preparations for use in the present invention.

EXAMPLE 3;

A composition is prepared as follows:
100 ml sterile isotonic saline solution
8.5 micromolar cytosine arabinoside Nerve regeneration is promoted by thoroughly bathing the injury site with the foregoing composition.

EXAMPLE 4;

A composition is prepared having the following ingredients:
100 ml sterile isotonic saline solution
0.1 mg hydroxyurea The foregoing composition promotes regeneration of damaged nerve tissue when administered directlly to the site of the injury.

EXAMPLE 5:

A pharmaceutical composition is prepared having the following ingredients:
100 ml sterile isotonic saline solution
0.2 mg 5-fluorouracil Nerve generation is facilitated when this composition is administered to damaged nerve tissue in quantities sufficient to bathe the injury site.

EXAMPLE 6:

Pharmaceutical compositions are prepared by adding to each of the compositions of Examples 3-5:
0.3 millimoles HEPES The nerve regeneration activity of each composition is superior to the activity of each composition without the addition of HEPES.

EXAMPLE 7:

Pharmaceutical compositions are prepared by adding to each of the compositions of Examples 3-5 the following:
0.3 millimoles TREA The ability of each of these compositions to facilitate nerve tissue regeneration is superior to the activity of each composition without TREA.

EXAMPLE 8:

A pharmaceutical composition is prepared as follows:
100 ml sterile isotonic saline solution
0.3 millimoles of TREA This composition, when administered to damaged nerve tissue in a living mammal, promotes nerve tissue regeneration.

EXAMPLE 9:

Pharmaceutical compositions are prepared by adding to each of these compositions of Examples 3-7 the following: 0.1 ml 3% hydrogen peroxide solution.

Each of the compositions, when administered to damaged nerve tissue in a living mammal, promotes nerve regeneration.

Although the foregoing invention has been illustrated by specific embodiments, various modifications and additions are encompassed by the present invention. Accordingly, the scope of this invention is intended to be measured only by the claims which follow and reasonable equivalents thereof.

What is claimed is:

1. A process for treating a mammalian nerve tissue injury creating an injury site environment more favorable to glial cell growth than to nerve cell growth which comprises modifying said environment to favor the growth of nerve cells.

2. The process of claim 1 in which the modification of said environment is accomplished by concurrently raising the injury site pH and retarding the proliferation of glial cells.

3. The process as defined by claim 2 in which the pH is raised by the administration of a buffer to the injury site.

4. The process of claim 2 in which the proliferation of glial cells is retarded by the administration of an antimitotic agent to the injury site.

5. The process as defined by claim 1 in which a pH within the range of between about 7 and 8 is established at the injury site and the proliferation of the glial cells is retarded by the administration of an antimitotic agent.

6. The process of claim 5 in which the pH is raised by administering a buffer to the injury site.

7. The process of claim 6 in which the buffer is ACES, ADA, AEPD, AMP, AMPD, BES, BICINE, BIS-TRIS, BIS-TRIS PROPANE, DEA, EPPS, MEA, MES, MOPS, PIPES, TAPS, TES, TREA, TRICINE, or TRIS.

8. The process of claim 5 or 6 in which the antimitotic agent is selected from the group consisting of cytosine. arabinoside, 5-fluorouracil, hydroxyurea, and methotrexate.

9. A process as defined by claim 2 in which the modification of the environment is accomplished by the administration of an antimitotic agent, a buffer and an oxygen supplying substance to the injury site.

10. A process as defined by claim 9 in which a pH between about 7 and 8 is established at the injury site, the proliferation of glial cells is retarded by the administration of an antimitotic agent and in which the oxygen supplying substance is a pharmacologically acceptable peroxide.

11. A process for promoting the regeneration of nerve tissue at a nerve tissue injury site which comprises administering an antimitotic agent to retard the growth of glial cells, a buffer to provide a pH between about 7 and 8, and an oxygen supplying substance.

12. A process as defined by claim 11 in which the antimitotic agent is cytosine arabinoside, the buffer is TREA, and the oxygen supplying substance is hydrogen peroxide.

* * * * *

UNITED STATES PATENT AND TRADEMARK OFFICE
CERTIFICATE OF CORRECTION

PATENT NO. : 4,868,161

DATED : September 19, 1989

INVENTOR(S) : Eugene Roberts

It is certified that error appears in the above-identified patent and that said Letters Patent is hereby corrected as shown below:

Column 1, line 5, after the title, insert:

--This invention was made with government support under Grant Nos. NS18858 and NS18859 awarded by the National Institutes of Health. The government has certain rights in the invention.--

Signed and Sealed this

Second Day of March, 1993

Attest:

STEPHEN G. KUNIN

*Attesting Officer*      Acting Commissioner of Patents and Trademarks